(12) United States Patent
Yang et al.

(10) Patent No.: US 7,837,111 B2
(45) Date of Patent: Nov. 23, 2010

(54) ELECTRONIC NUTRITION JOURNAL

(76) Inventors: Henry Yang, 425 S. Fifth St., Alhambra, CA (US) 91801; Christian Rodgers, 510 S. Resh St., Anaheim, CA (US) 92805

(*) Notice: Subject to any disclaimer, the term of this patent is extended or adjusted under 35 U.S.C. 154(b) by 508 days.

(21) Appl. No.: 11/973,077

(22) Filed: Oct. 5, 2007

(65) Prior Publication Data
US 2008/0083825 A1    Apr. 10, 2008

Related U.S. Application Data

(60) Provisional application No. 60/850,614, filed on Oct. 10, 2006, provisional application No. 60/928,127, filed on May 8, 2007.

(51) Int. Cl.
*G06K 15/00* (2006.01)
(52) U.S. Cl. .................... 235/462.13; 235/375
(58) Field of Classification Search ............ 235/462.13, 235/462.46, 375, 472, 487, 462.43; 705/14, 705/24, 27
See application file for complete search history.

(56) References Cited

U.S. PATENT DOCUMENTS

| | | | |
|---|---|---|---|
| 5,819,735 A | 10/1998 | Mansfield et al. ........... 600/300 |
| 6,129,276 A * | 10/2000 | Jelen et al. ................... 235/383 |
| 2002/0027164 A1* | 3/2002 | Mault et al. ............ 235/462.46 |
| 2002/0091569 A1* | 7/2002 | Kitaura et al. ................. 705/14 |
| 2005/0011957 A1* | 1/2005 | Attia et al. ............. 235/462.46 |
| 2005/0082370 A1* | 4/2005 | Frantz et al. ........... 235/462.25 |
| 2006/0111967 A1* | 5/2006 | Forbes ......................... 705/14 |

* cited by examiner

*Primary Examiner*—Edwyn Labaze
(74) *Attorney, Agent, or Firm*—Clifford Kraft

(57) ABSTRACT

An electronic nutrition journal that can include one or more portable units capable of reading barcodes and serving sizes on consumed food items either on menus or on items purchased. Portable units can communicate with either an intermediate computer or directly with a server computer that contains a master nutritional database relating nutritional data with bar codes. This master nutritional database can be updated by either user input such as user preferred menus or by visiting websites that contain this data. An external barcode generator can be operated to produce barcodes for commercial operations that sell food such as restaurants, food trucks, vending machines or others so that barcodes can be established for their menus or selections. The intermediate computer or the server can track food intake and provide computations of nutritional values, bench marks, etc. a particular user or for many users. The server and master nutritional database, as well as coding of restaurant menus, etc., can be run as a service that a user could subscribe to.

21 Claims, 8 Drawing Sheets

MASTER FOOD DATABASE — 58

| ITEM | BARCODE | NAME | NUTRITION INFORMATION | COMMENTS |
|---|---|---|---|---|
| | | | CAL. FAT SALT | |
| XXX 1 | USED UPC CODES | | | |
| XXXN | FREE UPC CODES | | | |
| YYY1 | USER DEFINED | | | |
| YYYM | FREE USER CODES | | | |
| ZZZ1 | BUSINESS DEFINED CODES | | | |

FIG. 7

ELECTRONIC NUTRITION JOURNAL

This application is related to and claims priority from U.S. Provisional Patent Applications 60/850,614 filed Oct. 10, 2006 and 60/928,127 filed May 8, 2007. Applications 60/850, 614 and 60/928,127 are hereby incorporated by reference.

BACKGROUND

1. Field of the Invention

The present invention relates generally to the field of nutrition monitoring and more particularly to an electronic nutrition journal system.

2. Description of the Prior Art

It is known in the art to monitor food intake. It is also known to create an electronic device that can scan barcodes on food packages and record or look up nutrition content. There are computer programs that track calorie intake as well as many other food parameters.

For example, Mansfield et al. in U.S. Pat. No. 5,819,735 teach a portable, autonomous electronic device with a barcode scanner and a database that allows a user to scan barcodes on food items consumed and keep a cumulative total of calories and other nutrients. They also teach that foods that are used in cooking may be referenced by scanning generic barcodes provided with the device. Mansfield et al. also teach a handheld device with a display screen that can display histograms of items like carbs, fats, sodium and other food ingredients.

Shepley in U.S. Pat. No. 5,478,989 teaches a device that compares nutritional information from a barcode scan of a food product with the personal health data of a user. Shepley primarily teaches a device that aids in selecting food items.

These prior art systems generally emphasize an autonomous device that tries to be self-contained with a microprocessor and onboard database. A particular problem with this is that it is very difficult to keep the database up to date with the variety of new food products entering the market. It is also difficult to make meaningful calculations or perform long term tracking of nutritional intake with small, totally handheld devices. Usually, the local database becomes quickly out of date, and because of limited memory capability, it is not possible to retain large amounts of data taken over periods of a year or years.

It would be advantageous to have a system that allowed a user to scan barcode information from food items, enter serving sizes, and enter data about food products like vegetables and fruit, and then upload this data into a personal computer or wirelessly over the internet to a more comprehensive program that has access to a large database of food items and ingredients. The larger database could maintain records of nutritional intake and track them for as long as the user desired. The larger, more comprehensive database could be kept up to date by either the user, interested parties or the food companies themselves, or could be managed by a nutritional journal provider.

SUMMARY OF THE INVENTION

The present invention relates to an electronic nutrition journal that can include a portable unit with a barcode reader, or user defined code reader, for scanning and collecting bar or user defined codes from food packages or items, meals, restaurant menus and publications, and user defined food items or meals. The invention can match coded food items with their corresponding nutritional content information using a master nutritional database located either on an intermediate computer or a server. The system includes the ability for users to enter serving size information or other identifiers such a points systems, etc., to more accurately calculate nutritional information of the food consumed. The electronic nutrition journal provides a convenient and easy way for an individual to track his or her nutritional intake. The codes may include UPC codes or any industry or user defined code used for the purpose of identifying a food item or meal a user creates on his or her own or buys at a super market, store, warehouse, or restaurant. A user defined code can be supplied to the user by the system when a user wishes to make a personal definition of a food item. The user may use the code to identify a particular food item, meal, or food creation and its nutritional content. The user may enter serving size or point information using an input interface. The scanned or collected bar code information along with predefined or user defined serving size or points information can then be downloaded or transferred to a different hardware platform in order to match the food items and their specific nutritional content. This transfer can be to a personal computer, laptop computer, PDA, cellular telephone, personal music player, or any other electronic device, or to an internet website on a server owned by a nutritional journal provider. All transfers can optionally take place wirelessly or using partially wireless links. The server can maintain a database of food items and their corresponding nutritional information, as well as continually updating its master database with new information. This nutrition information can also optionally reside on a user's PC or other computer. Software at the user's computer, and/or PDA can be used to add up the total calories and any additional nutritional information collected from the barcode reader and the nutrition database. This information can be stored allowing the end user to track, run reports, print information, and/or save nutritional information collected. Additional software can be available for a user to create his or her own coded food items, so that upon swiping or collecting the code, the downloaded or transferred information will be match with user defined food items and their corresponding nutritional information.

The master nutritional database can be updated by receiving data from an external barcode generator that can receive food menu data either directly from users or from restaurants, food trucks, vending machines or any other source of food information. The server application software can also automatically update the master nutritional database by visiting various websites that contain nutritional data.

DESCRIPTION OF THE FIGURES

Attention is directed to several illustrations that aid in understanding the present invention:

FIG. 7 shows an embodiment of a master nutritional database.

Several drawings and illustrations have been provided to aid in understanding the present invention. The scope of the present invention is not limited to what is shown in the figures.

DESCRIPTION OF THE INVENTION

The present invention relates to an electronic food journal by which a user can use a portable handheld unit to scan food items, enter service sizes or codes and generally gather data about what is being eaten. The portable unit can either wirelessly, or by cable, transfer this data to either a personal computer, PDA, cellular telephone or any other electronic device or to a remote server or elsewhere via a communications controller.

The portable unit can be configured to read standard UPC bar codes, code 128, 2-dimensional codes and any other code. With this capability, the present invention is not limited to just the UPC codes on packaged food products. With a wide range of code capability, the invention can capture and identify most existing food items.

Figure 1A:
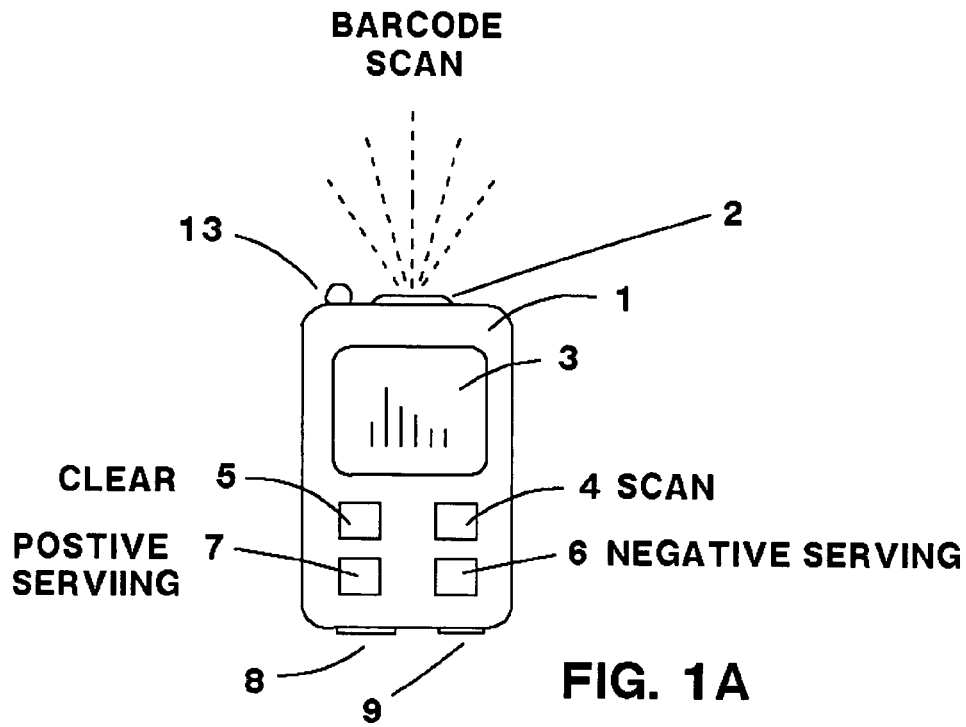
FIGS. 1A, 1B and 1C show different embodiments of a portable unit of the present invention.
Figure 1B:
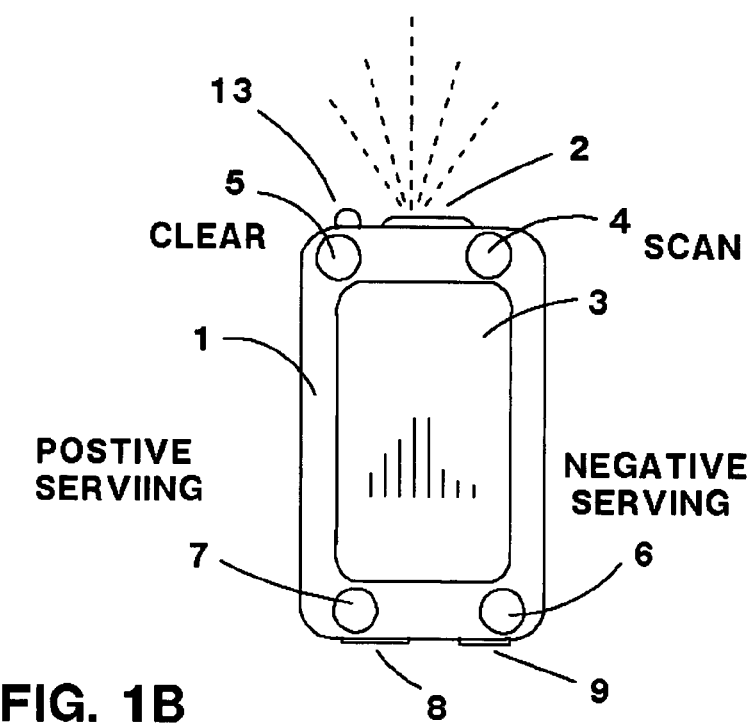
Figure 1C:
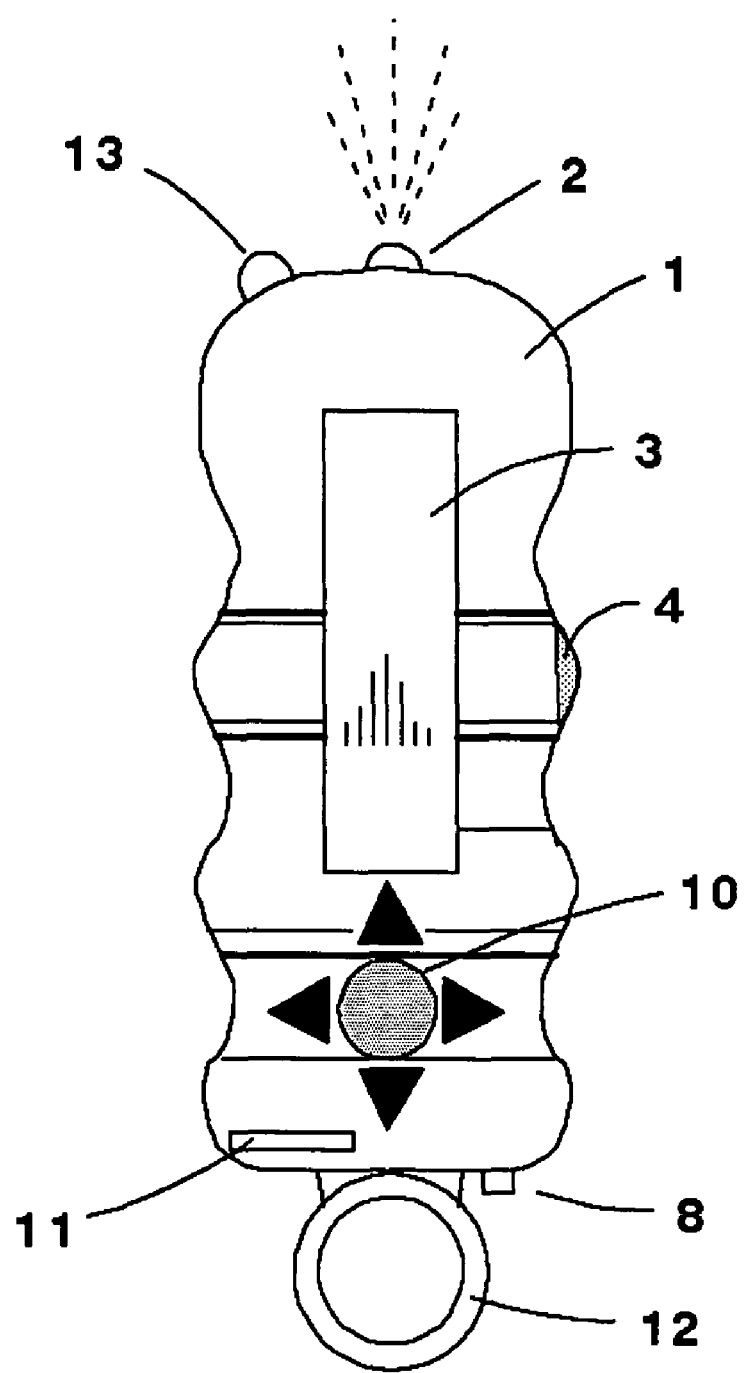

FIGS. 1A, 1B and 1C show different possible embodiments of the portable unit. A housing 1 can contain a bar code scanning device 2 and a display screen 3. Several buttons 4, 5, 6, 7 can be used to collect food data. FIG. 1C in particular shows an embodiment of the device that is designed to operate as a key chain dongle or FOB, or simply be carried on a key chain. An antenna 13 can be used for wireless transfer of data. This antenna 13 can be external or internal to the device. The device can contain any of several known methods of wireless access including a cellular telephone, WiFi as well as a standard cable access 9 or a USB port 11. The display screen 3 can be liquid crystal known in the art, or any other type of display device. The device can contain an internally battery with a charger port 8 similar to those of cellular telephones. Generally control buttons on the device can be a scan button 4, clear button 5, positive serving button 7 and negative serving button 6. Other buttons or controls of any type are within the scope of the present invention. In particular, FIG. 1C shows a 5-way button or joystick 10. This figure also shows a key chain coupling 12 that facilitates attachment to a key chain.

In particular, the buttons for changing the serving size 6, 7 can be used by holding the positive serving size button 7 to increase the size, and the negative serving size button 6 to decrease the size. It should be noted that serving sizes can be optionally entered a either an absolute quantity, or as a percentage of the item eaten, as well as possible the relative size of an item. For example, an apple might be listed as small, medium or large with a percentage eating such as ¼, ½, all, etc. Any way of entering serving sizes is within the scope of the present invention.

As will be explained, the portable part of the present invention can contain a processor, memory and can optionally perform some nutritional computations. It is possible to use an embodiment that simply collects data and transfers it, or a more sophisticated mode that not only collects data, but displays some nutritional information on the screen at the time the data is collected. The unit may also allow optional transfer of data to more than one remote site or to several remote sites such as a personal computer and a remote website. The portable unit may optionally contain a database.

Figure 2:
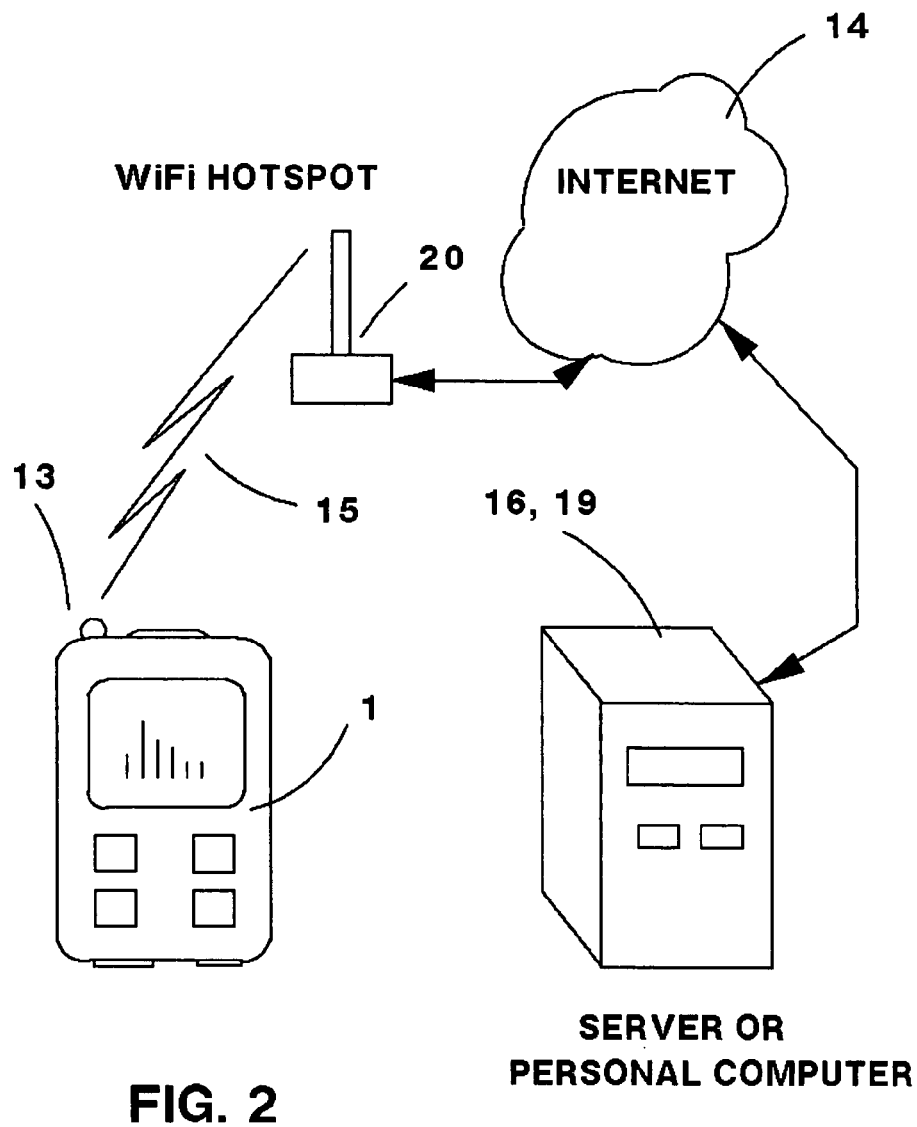
FIG. 2 shows a block diagram of a simple system with a portable unit and a remote fixed part.

FIG. 2 shows a portable part 1 with a barcode reader 2 transferring data wirelessly 15 to a WiFi access point 20 or by cellular telephone over the internet 14 to a server 16 or personal computer 19. Here data can be simply collected by the portable unit such as bar codes and serving sizes, but is not normally processed in the portable unit. Some embodiments of the portable unit can provide real-time feedback of the nutritional values of food items entered from the barcode reader using a local database. All of the data in the portable unit can be passed to the remote server for tracking and processing. The detailed operation of the server 16 will be subsequently discussed.

Figure 3:
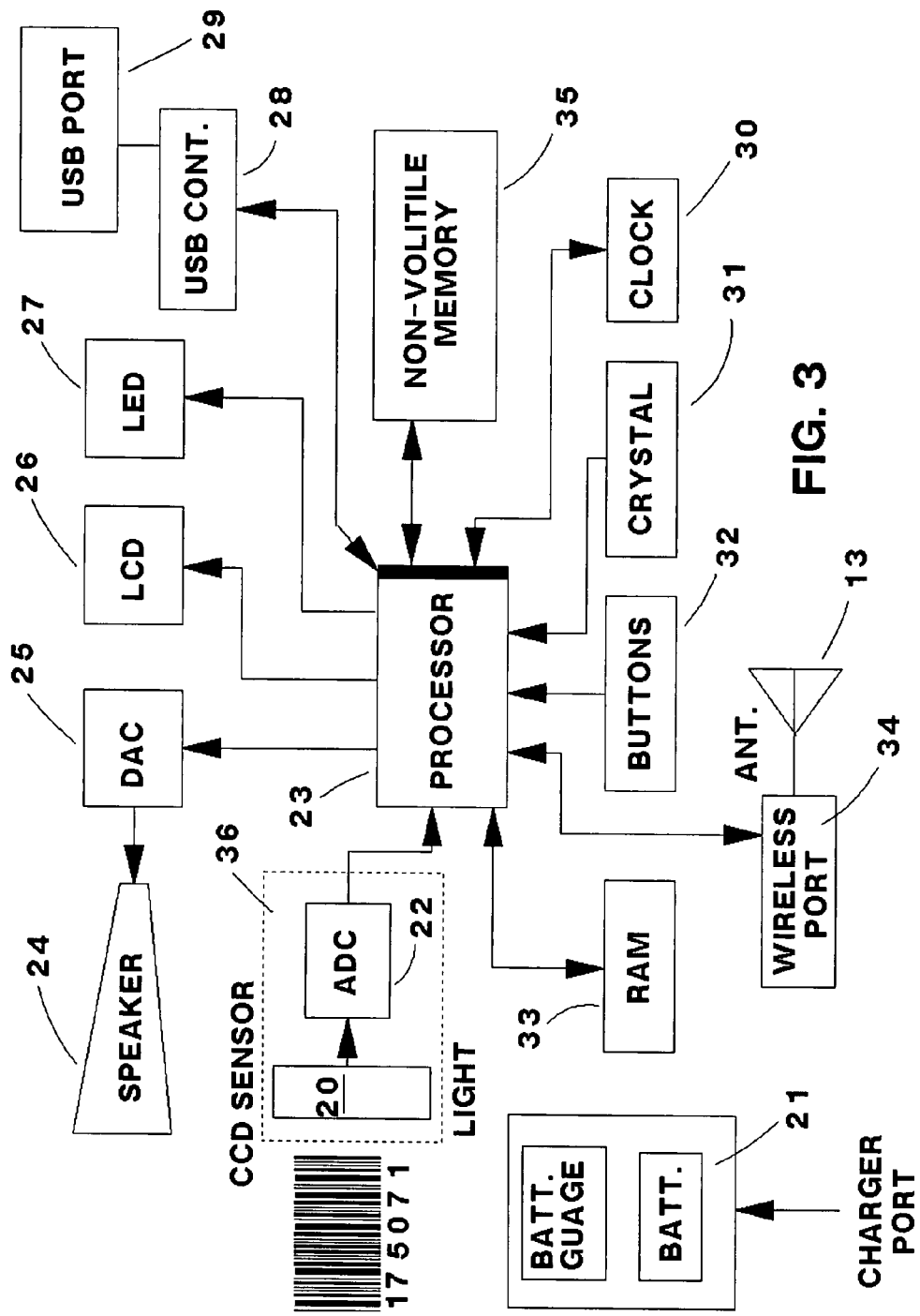
FIG. 3 is a block diagram of an embodiment of the portable unit.

FIG. 3 shows a block diagram of a typical embodiment of the portable unit of the present invention. The processor 23 can be a microprocessor, microcontroller embedded processor or any other type of computer or processor. This processor 23 controls an optional speaker 24, digital to analog converter (DAC) 25 to drive the speaker, a liquid crystal or other display 26 and optional LEDs 27. The processor 23 is also normally connected to a memory 33, switches or buttons 32 and a processor clock crystal 31 or oscillator. An optional battery-powered real-time clock 35 can also be provided. A barcode scanner 36 can contain an analog light reader such as a charge-coupled device (CCD) or other light sensor 20 which drives an analog to digital converter (ADC) 22 to convert raw scan voltages to digital words. The ADC 22 normally feeds these digital words into the processor 23 by methods known in the art. It is within the scope of the present invention to have the ADC be part of an OEM barcode scanner 36. The processor 23 also can drive a USB controller 28 and a USB port 29, or any other cable port such as Ethernet or any other communications method. The processor can optionally drive a radio or other wireless communications circuit 34 and an antenna 13 if the wireless circuit uses radio frequencies. The wireless communications port can be a WiFi port, cellular telephone link, Bluetooth link, infrared light port or any other wireless port or communications method. The circuit shown in FIG. 3 is simply an example of many different circuits that could be used to form the portable part of the present invention. Many other variations are within the scope of the present invention.

Returning to FIGS. 1A-1C, it will be realized that certain software resides on the portable handheld units shown. As shown in FIG. 3, each unit contains a microprocessor, microcontroller or other CPU 23 that can process instructions from a memory. These instructions are in the form of software that resides on the device preferably stored in a non-volatile memory 35. This software is used to read bar code information from a barcode reader 36 previously discussed, read switches and buttons 32, drive the display 26 and control a wire communications port 28 and optionally a wireless communications port 34. This software is normally used to store read-in data temporary, in some cases, manipulate it, and to transfer it over one of the communications ports to a remote server or other computer remote from the device. In addition, this software allows entry of serving sizes, and in some models such as the embodiment shown in FIG. 1C, the software allows real-time calculation of the total nutritional values of foods consumed such as total calories, fats, carbohydrates, etc. This latter computation can be based on an optional local database stored in the unit.

Figure 4:
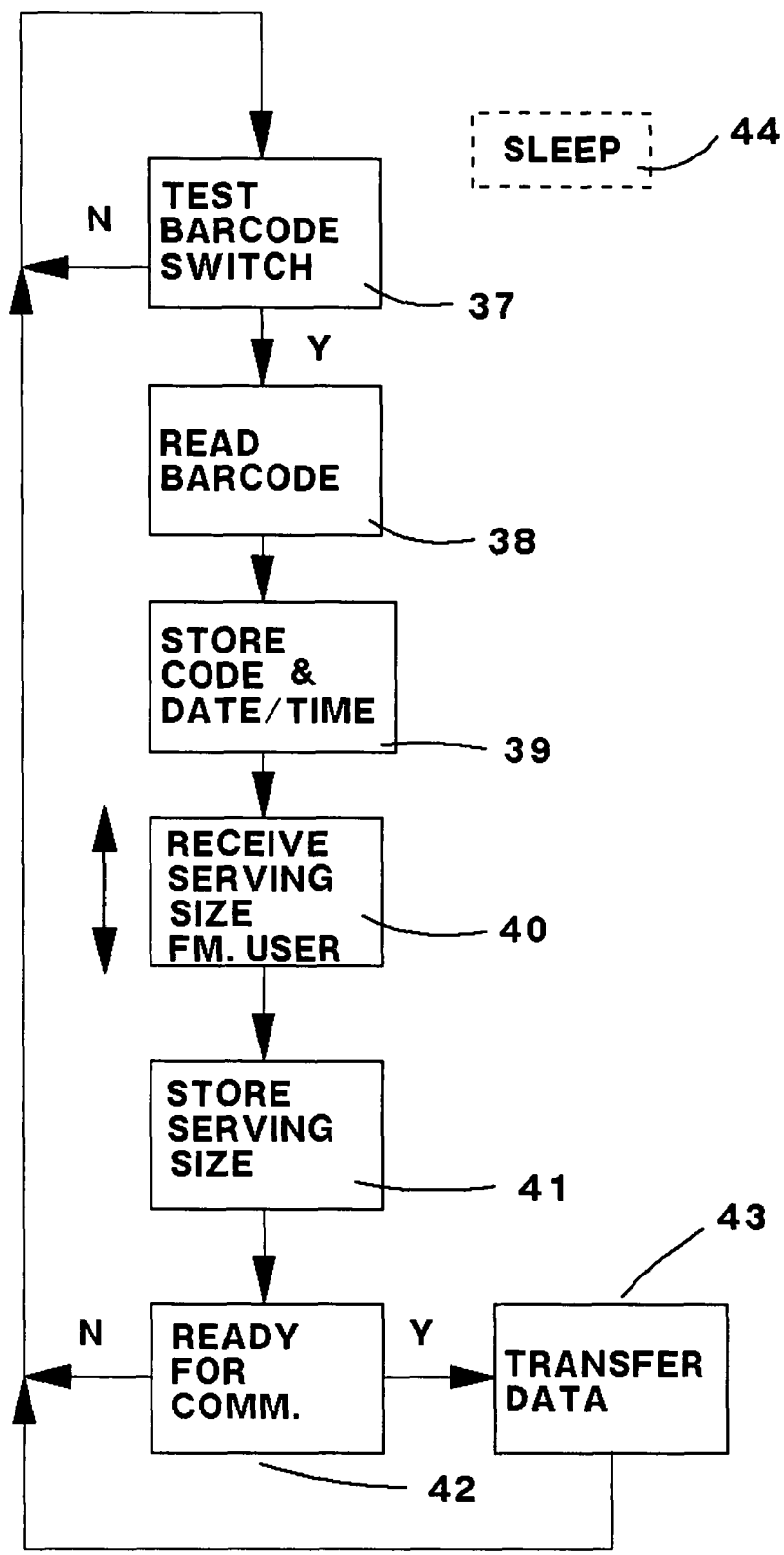
FIG. 4 is a flow chart of an embodiment of software for a portable unit.

Typical operation of the software in the local handheld unit can be seen by referring to FIG. 4. Starting at the top of FIG. 4, the CPU tests 37 the barcode switch. If it is not depressed, the system tests if ready for communication 42. If not, the system tests the barcode switch again. This cycle repeats until the user either orders a barcode scan or indicates that transfer of data is desired. When the barcode switch is activated, the system reads a barcode 38 and stores it with a date and time stamp 39. The user is then ask to enter a serving size 40. The CPU can put up a standard serving size on the display, and the user can adjust upward or downward from that with up and down buttons. This operation can also be done from a menu. After the serving size is entered, it is stored 41 and the CPU can test if communication is desired 42. A loop similar to this can be executed indefinitely. The unit can power-down and go into a sleep mode 44 known in the art when not in use for a predetermined time. The unit can wake-up again when one of the buttons is pushed.

Different embodiments of the portable unit can also be used to swipe or scan barcode information from food items that are not going to be consumed, but rather are desired to be entered into various databases in the system. Optionally, this data can be made available for immediate display on the portable unit.

Figure 5:
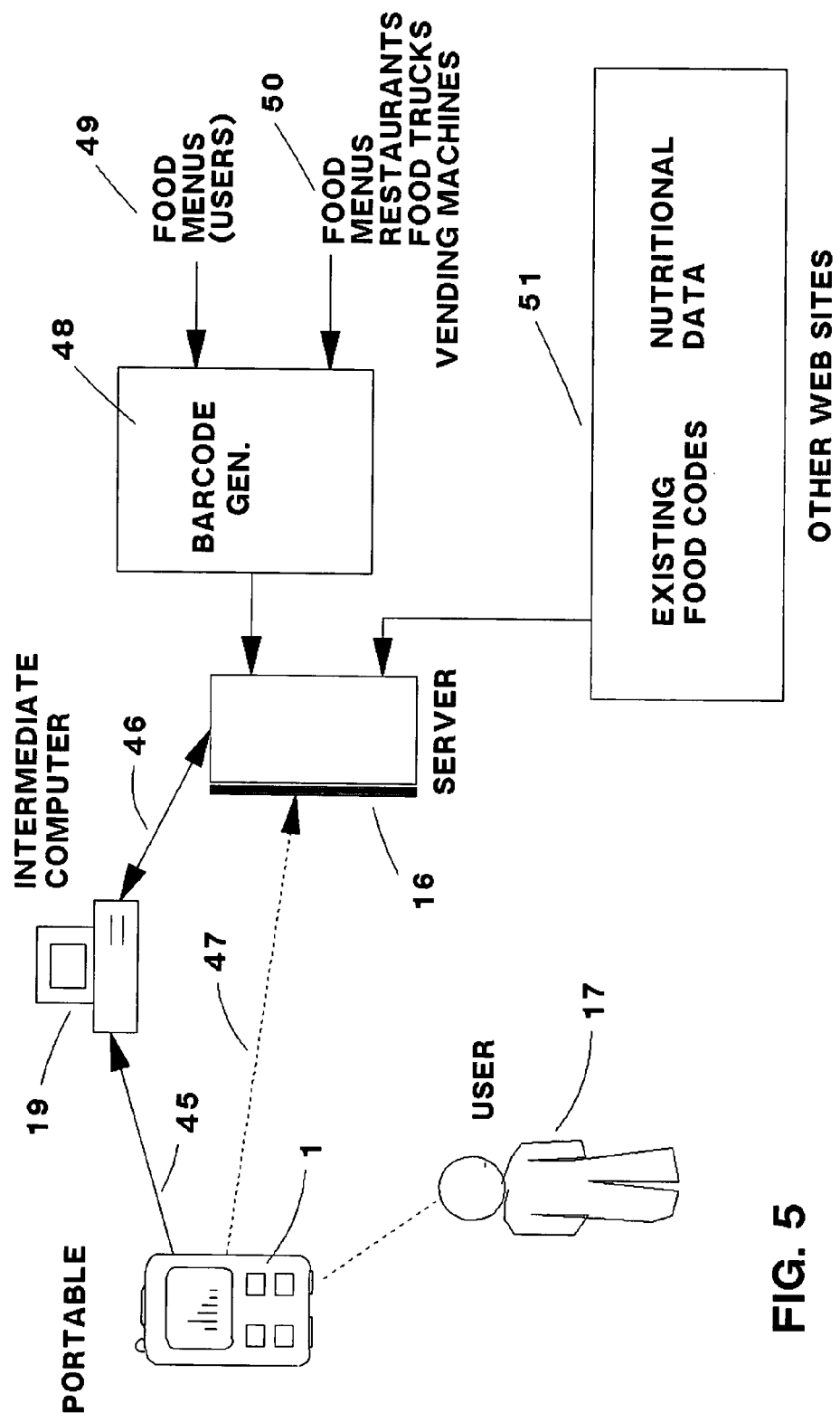
FIG. 5 shows a block diagram of a more complex system with an intermediate computer.

Turning to FIG. 5, a network version of the present invention can be seen. A user 17 can communicate with a local unit 1 as just described to collect barcode data on food consumed as well as serving sizes. This collected data can be transferred either to an intermediate computer 19 or a remote server 16. The remote server 16 can be operated by a nutritional information provider and run one or more websites for that purpose. The intermediate computer 19 can be a personal computer, a laptop, a PDA, a server or any other type of computer. This computer can contain resident software that executes on it as known in the art that can include a database that can store nutritional content data from the government (FDA), restaurants, food manufacturers, food producers, nutritionists, publications or any other source of nutritional data. The software resident on this computer can calculate, bench mark, store, process, manipulate and print out nutrition information on food items.

It should be noted that in an optional embodiment, this software could also reside and execute on a portable unit. However, because of the possibly large amount of data, and the desirability to be able to print out this data, it is preferred to have this software run on a separate, remote computer 19. This software can also reside on the server 16; however, in a preferred mode of operation, the server 16 may be remote from the user and/or possibly belong to another entity such as an electronic journal information provider who makes sure that the master database on the server is always up to date and reflects the latest in knowledge about nutritional content and nutritional needs of users. This server can contain all known food barcodes and make them available as a code library to all users of the system. The process of creating a master nutritional database on this server may be automated and/or manual. The preferred mode is that an initial database is created manually, then application software on the server searches for other items and information not already in the database. New food items that are discovered by users or by whoever manages the server can always be entered manually.

Continuing to examine FIG. 5, the intermediate computer 19 can itself be a handheld unit such as a PDA or cellular telephone. It should also be noted that the intermediate computer 19 and/or the server 16 can communicate with and accommodate more than one portable unit. An example of this might be each member of a family having a portable unit that feeds data into a single intermediate computer 19. In the case of the server 16, it could be operated by a nutritional information provider and accommodate many portable and intermediate computer users.

The communications link 45 between the portable unit 1 and the intermediate computer 19 (or the server 16 directly with a link 47) can be wired or wireless. When intake information from a portable unit is transferred to the intermediate computer 19, software on the intermediate computer can use this data to update a particular user or family member's personal food intake database. This software can match bench marks, keep running totals of intake of various nutrients, report any noted deficiencies of vitamins, minerals or other essential food elements, print periodic reports, and generally maintain a personal nutritional database for each user of the system.

The server 16 can generally be a remote server as previously stated that communicates with the intermediate computer 19 or portable units 1 directly over links 46, 47 which can be any type of communication link into a network. In particular, these links can be network based links into the internet through numerous means known in the art. These links 46, 47 can be wired, wireless, partially wired and partially wireless, WiFi, cellular telephone, landline telephone, or Ethernet into any type of internet or intranet or LAN access. The only requirement upon these communication links is that they allow two-directional communication between either the intermediate computer 19 or one or more portable units 1. This communication allows transfer of nutritional data from the server 16 to the intermediate computer 19 or portable unit 1, and communication of food intake data to the server 16 if desired.

The remote server 16 can run application programs and provide access to stored databases as is known in the art of servers. In particular, the server 16 can contain a database that also stores and gathers nutritional and other information from the government, food experts, nutritionists, websites and other private and public entities that publish nutritional content information. This database can also receive data from a user's database on the intermediate computer 19 and on portable units if desired. The server 16 can also receive data from other sources such as a remote or local barcode generator 48 that can generate internally used codes (or external codes) for such things as user's food menus 49 and food menus 50 from restaurants, food trucks, vending machines and any other source of food information. Communication between the server 16 and barcode generators 48 or other sources of barcodes can be network based or any other means of communication.

The server 16 can also contain software that performs web-crawling or searching functions to find new sources of nutritional data and can contain lists of known websites 51 that can be used to continually update its internal nutritional database. In this manner, the server's database can automatically and continually be kept up to date. These known websites 51 can be visited on a regular basis so that the master database on the server 16 is always as up-to-date as possible. Application software on the server 16 can be provided that resolves conflicting data about a certain food item. This can be done automatically using artificial intelligence or logic methods known in the art, or user intervention can be requested. A user can be informed when such a conflict is resolved automatically.

The operation of the preferred embodiment of the system of the present invention will now be described. This description is simply an example of ways the system can operate. One skilled in the art will realize there are many possible variations. These variations are within the scope of the present invention.

The operation of the software in the portable unit has been described previously and shown in the flow chart of FIG. 4. Fundamentally, the portable unit scans barcodes and stores these codes along with serving sizes and the date and time when the scan occurred. The steps in this process can be:
1. Swipe or scan bar or user defined code.
2. Confirms it is a valid code. If not, issue an error message.
3. Issue a serving size prompt to user.
4. Collect serving size from the user either by having user directly enter it, or by having the user manipulate buttons to generate it on the display.

5. Apply a time and date stamp to the data.
6. Store the scanned code along with the serving size and the date and time.
7. Wait to scan the next code.

Optionally, on some of the embodiments of the portable unit, nutritional information can be displayed on the screen. This could include calculated information such as total calories, total fats, saturated fat, sugars, sodium, etc. Also, the portable unit can contain a delete option for deleting an erroneously scanned item.

In other embodiments of the portable unit, the device can first display daily or total nutritional data in its journal along with the unit status such as battery status, time, date and other data. This presentation could be controlled or set up with a setup menu. After an item is scanned, the device can display information such as an image of the item, product name and nutritional information. The number of items, and what they are (such as sugar, fat, etc.), can be defined by the user using the setup menu.

It should be noted that not all food items consumed (in fact many) do not contain a barcode that can be immediately scanned. For example, if the use consumes and apple or lettuce, there may be no barcode to scan. It is an optional feature of the present invention that the portable unit allows entry of such items as intake. There are at least two different ways this can be done: 1) the device could provide a list of commonly used but uncoded food names along with their pre-defined bar codes (e.g. apple or by barcode number, lettuce, etc) and 2) the user could enter the item by name rather than scanning it. In the latter case, the name could be either directly transmitted or could be assigned a temporary code to be transmitted. Serving size and date/time would be handled as in the scan case.

In those embodiments of the invention where the portable unit contains a database, this database can be downloaded from either the intermediate computer 19 or the server 16 as previously described or from any other source. This download can be automatic upon connection or user-requested.

Whenever the user desires, the stored scanned codes, along with serving sizes and time/date stamps can be uploaded over the communication link to either the intermediate computer 19 or directly to the server 16. This can be initiated by connecting a USB or other communications cable to the portable unit or by initiating a wireless connection from the portable unit into either the internet, to a local wireless receiver or to a wireless device like a PDA or cellular telephone. The portable unit can optionally contain a cellular telephone.

Once the data is transferred from the portable unit to either the intermediate computer 19 or the server 16, the collected codes can be matched with specific food items in the database residing on the computer or server so that nutritional information can be entered into the user's personal profile or file (user database) on the intermediate computer 19 or the server 16. The software on these devices can be used by the user to then compute profiles, total intake of various nutritional items such as calories, vitamins, etc. and print or further forward reports or graphs of running totals and results. Authentication, authorization and access control known in the art can be used for secure communication between the portable unit and either the intermediate computer 19 and the server 16 or both.

Application software on the server 16 can generally collect and store government, industry, expert, restaurant and user defined food items, as well as user defined codes as well as matching nutritional information for each food item and/or code. This software can optionally search and upload data from the intermediate computer's database or even from any database on the portable units. This search can be made for newly defined food items and/or codes and their corresponding nutritional content. The contents of this master database conversely be made available, either in whole or in part, to the intermediate computer 19 and/or any portable unit. This can be done during routine data transfer connections or on a periodic schedule (if there is a persistent connection say with the intermediate computer). The update of other databases from the master database on the server 16 can be set by the user to be automatic upon connection or by request only.

Figure 6:
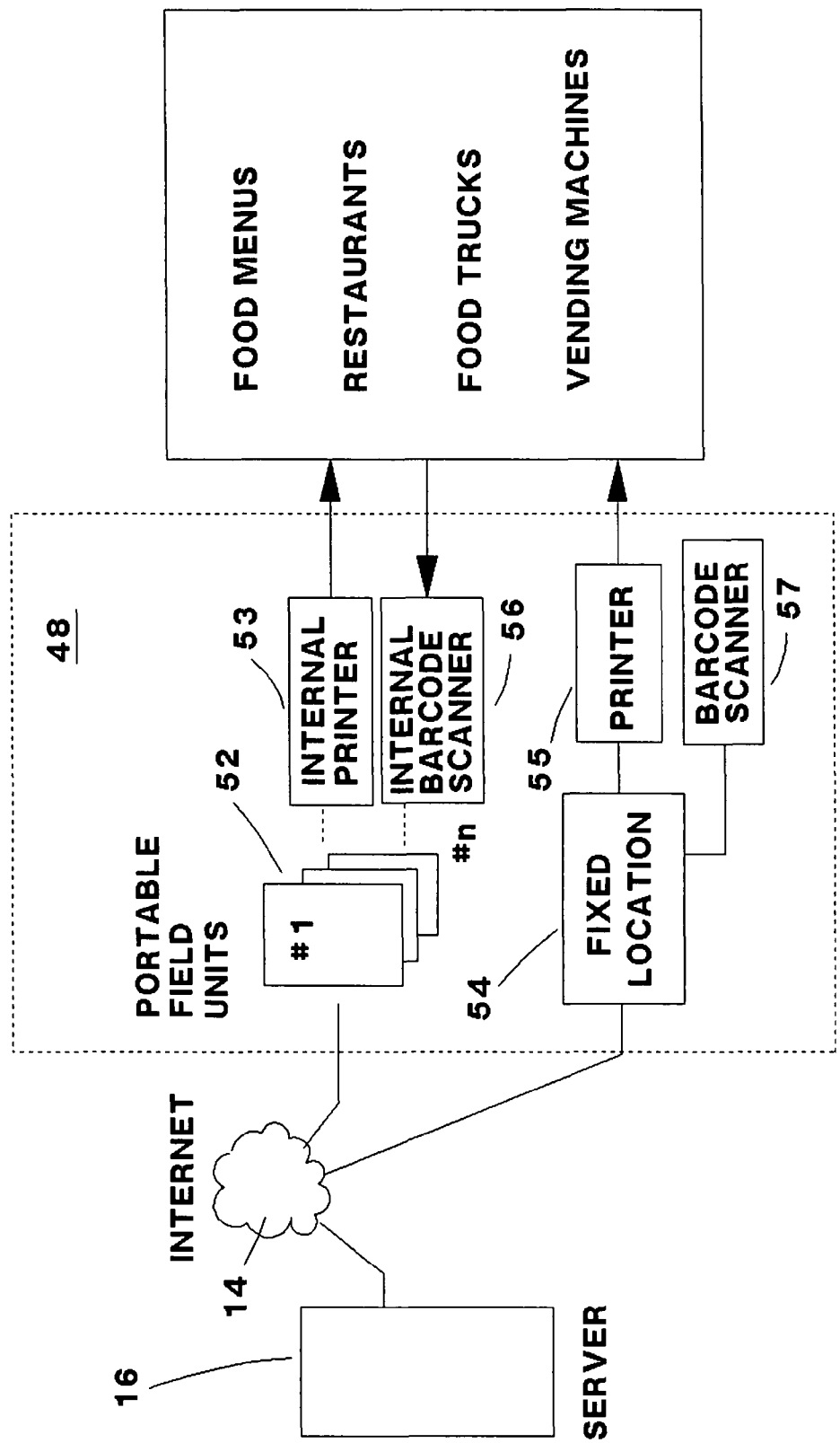
FIG. 6 shows details of portable and fixed barcode generators.

As shown in FIG. 5, the server computer 16 can be connected via the internet or other communications means to a barcode generator 48. This can be any standard hardware known in the art that generates barcodes. Its main function is to generate barcode labels for any new food items found in food menus 49, food menus 50 from restaurants, food trucks, vending machines and other sources, and to provide the server with the newly assigned food codes and their corresponding nutritional values. As depicted in FIG. 6, the barcode generator can consist of one or more portable handheld units 52 and stationary terminals 54 with each having the following capabilities:

1. network functionality with the server that allows data collection and processing in real time
2. connection to an internal barcode scanner 56 or external scanner 57 that allows instant look-up of barcode information
3. connection to a built-in printer 53 or an external printer 55 that allows the printing of barcode labels
4. use of third-party software platforms and custom software applications.

The external barcode generator 48 can be hand held and/or be part of stationary terminals that contain hardware and software (using a processor). The portable handheld barcode generators can be used by the field personnel of the nutritional provider for a small fee service to code food menus for any food service such as a restaurant, food truck, vending machine or any other food service. As a cheaper alternative, the fixed or stationary terminals can be used by the office personnel to code food menus. The software normally generates a unique barcode for each item entered along with its nutritional information, and then transfers that newly entered information to the master nutrition database on the server 16. The process entails inputting a new food item from a menu or other source, generating and optionally displaying a unique generated barcode, storing the barcode locally, collecting any extra information about the item that should be in the database such as user-entered nutritional information, and transferring the new barcode along with the information to the database on the server 16 in real time. The transfer can be a push operation known in the art, or the barcode generator 48 can wait for the server 16 to request new information from it. The barcode generator 48 can also contain an internal printer 53 or the interface capability to an external printer 55 that allows physical printing of new barcodes. This feature can be used to generate sets of codes that can be used for items that normally don't carry barcodes. The barcode generator 48 can generally be remote from the server 16 and preferably communicates with it over the internet or other communications means. However, it can optionally be connected to the server 16. In addition, the barcode generator can contain an internal barcode scanner 56 or the interface capability to external barcode scanner 57 that allows instant lookup of barcode information against the master database on the server. As a note, the functions of the barcode generators are transparent to the users on the network system since the task is managed by the nutritional provider.

The need for the user to be able to have personal barcodes and share them with other users is crucial in attracting new users to the system. As previously discussed, the server 16 may belong to a provider or other entity. In fact, the user may pay a fee to use the service. The user may disagree with a particular nutritional value in the master database, or the user may have some special way of defining nutritional information about a particular item, or simply want an item that for some reason does not appear in the master database. As also shown in FIG. 7, the master database 58 that is available all users in the system resides on the server 16. Additional servers and multiple firewalls and network security known in the art may be used to safeguard this master database against viruses, hackers, or natural disaster. The master database can contain three or more types of codes:

1. UPC food codes—These are a subset of the food code used in the present invention, thus making the new system compatible with existing and new UPC food codes (i.e. system will be able to recognize existing food UPC codes). These codes are free to all users in the system.
2. User-defined codes—The system will allocate a predefined section of the available code space for users in the system that enables each user to reassign this code for his or her personal use. A predefined set will be available free to each user, but additional codes may optionally be purchased for additional fees. For example, the server may allocate ten free codes to each user in the system. The user may then assign any of these codes to his personal meals. If he needs more codes, he can purchase them at a reasonable price or optionally, the system could supply them free on demand. If a user cancels his subscription service, the codes can be returned to the users' predefined pool for reassignment to new users in the system. This code and nutritional information once accepted by the server will be available to other users on the network if desired. Users of the system will normally be responsible entering the nutritional content and maintaining the assignment of these assigned codes in the system. However, the server may reject the new food assignment request if it believes that it contains bogus data or is simply wrong for some reason. For example, Joe's hamburger has 9,999 calories.
3. Business codes—These codes can be used by the code generator to code meals and food menus from restaurants, food trucks, cafeterias, vending machines and the like. As stated earlier, the nutritional provider can provide this service for a small fee to food establishments to generate the barcodes for their food menus and corresponding nutritional values, or provide the service for other food items not in the master nutritional database. Users of the system can then scan these barcodes for their nutritional tracking when eating at these food establishments. Alternatively, a business could purchase a set of these codes to define their food items. For example, McDonald's could purchase 100 of these codes and assign them to their food items according to its wishes. However, the new assignment, along with its nutritional content data, must be also entered into the master nutritional database. For a small fee, this could be done using the internet or other communication methods as in the case of the user's predefined code where the nutritional data are entered manually and maintained by the user (e.g. via a website), with the assistance of a nutritional provider's personnel (e.g. email or telephone calls of food assignments and nutritional values), and automatically via proprietary software (e.g. web crawling that monitors for changes in a food establishment's website).

Additionally, the master nutritional database should have at least the following fields for identifying each food item: food item number, barcode in alpha and/or numeric representation, nutritional information such as food name or description, fat, sugar, calories and other nutritional contents, and comments. An example of the master nutritional database is shown in FIG. 7.

When personal barcodes are used, the server can identify which user, either of a particular intermediate computer 19, or of a particular portable unit is entering the code. Whenever the user scans or enters that particular code, only that user receives the nutritional information associated with it. For this reason, it is important that the server 16 has the ability to associate a particular user with a newly generated barcode. As stated, the server and or the database can also be managed or provided by the nutritional provider for the user (for example on a website). As stated, the provider can optionally accept subscriptions from users.

Concise Summary of the Present Invention

We will now provide a concise summary of the hardware and software components that make up a typical embodiment of the present invention along with typical modes of operation:

H1 and H2 Hardware Components:

Portable hardware such as that shown in FIG. 1A can be called H1 hardware. H1 hardware can include a display screen (LCD), a button 4 to initiate a scan or bar code reading, a button 5 for deleting a scanned item from the H1 memory, and two buttons 6, 7 for changing the serving size as has been described. H1 hardware may also include menu driven software along with a more advanced button system (e.g. a 5-way joystick) that allows user to delete and enter serving size or points information. H1 hardware can connect to a hardware or wireless link that connects the H1 hardware to a computer or computer system in order to download or transfer the collected bar or user code, serving size and system information.

S1 Software:

Residing in the H1 hardware, S1 software can be used to manipulate, save, process, and store data downloaded or transferred data from the H1 hardware through the communications link.

S2 Software (Client Application/Database)

S2 software, which can reside on either an intermediate computer 19 (which can be a PC, PDA, laptop, cellular telephone, or other device or a server) can include a database that can store nutritional content data from the FDA, restaurants, food manufactures and food producers, nutritionists, or any other publication or credible source. S2 software receives this nutritional information from a server 16 and S4 software residing on that server. The server 16 with S4 software connects to S2 software via the Internet or other network connection (e.g. CATS cable using DSL service, telephone cable via the phone line service.)

The information in this database can be matched with the collected bar or user defined code and the corresponding nutritional information of the food items. S2 software also can create user specified reports and can calculate, bench mark, store, process, save, manipulate, and or print the nutrition information for the food items. S2 software may reside on a personal computer or processing system, the H1Plus hardware system or a third party computing system, i.e. PDA, personal music device, or cellular telephone.

H1Plus Hardware

Hardware such as that shown in FIG. 1B can be called H1 Plus hardware. In addition to all the functionality provided in H1 hardware, H1Plus hardware allows the user to swipe or scan and collect bar or user defined codes and display nutritional information along with nutritional calculations at the time of collection on its display screen. H1Plus hardware can process, calculate, store, manipulate, bench mark and save nutritional information using the S2 software. This information can be made available for the user to view directly on the H1 Plus display screen.

H1PlusPlus Hardware

Optional hardware such as that shown in FIG. 1C could be called H1PlusPlus hardware. In addition to providing real time display of nutrition information it can provide additional features such as a user friendly menu and a 5-way joystick. The user can press a button and system is ready to use.

S3 Software (User Defined Codes and Nutritional Content)

S3 software can reside on an intermediate computer 19 and can be used to create user defined codes for food items or meals. An S3 user can use the software to create and print their own food labels or coding system which can be read by H1 or H1 Plus hardware and matched to user defined nutritional content saved by the user on an S2 database. S3 software is designed for home or restaurant or other commercial/consumer use.

A user of S3 software can code food items, meals or food creations so that H1 or H1Plus users will be able to collect the code and using an S2 database and match the code with the nutritional content of the food item, meal or creation defined by the S3 user.

H3 Hardware (Third Party Hardware Platforms)

H3 hardware can be a third party hardware platform that will download or transfer collected food item codes from H1 hardware. H3 hardware may also contain an S2 database to match food items and nutritional content with the collected codes from H1 hardware. The third party hardware platform can include any of the following: cellular telephone, computer, PDA, personal music player, television, and any other hardware system with a display screen. H3 hardware may also include a scanning system in order to scan and collect bar or user defined information. If used in this way, H3 hardware can replaces the specific user's need for H1 or H1 Plus hardware.

H4 Communication System

The H3 hardware can use a communication system to connect the server 16 and the S4 database to the S2 database and H3 hardware. This communication system can use a web or networked based connection in order to transmit and receive data from the client. The client in this case would be the S2 database and/or the H3 hardware.

Server and S4 Nutrition Information Database

The server 16 normally houses the S4 application database. S4 software and the server 16 are normally used to gather nutritional and other information from the FDA, food experts, nutritionists, web sites and other private and public entities that publish nutritional content information. The S4 database stores, updates and collects this information. The server 16 and the S4 database may also receive data from a user's S2 database, the barcode generator (H7 and S5), and H8 public food code and nutrition web servers. In addition, the S4 database may receive and/or send user defined codes and food items from S3 users.

H6 Hardware (Third Party Hardware Platforms)

A communication system that can be called H6 hardware can connect a barcode generator (H8 and S5) to H5 server and S4 database and/or H8 public food code and food nutrition web servers. The H6 hardware can use a web or networked based connection for data communication.

H7 and S5 (Barcode Generator)

A server that can be called H7 hardware houses the S5 application software. S5 software and H7 can be used to generate an internal code for each menu or user's defined food item and its corresponding nutrition data.

H8 Hardware (Public Food Code and Food Nutrition Web Servers) H8

H8 hardware represents third party public food code and food nutrition web servers.

Operation

H1, H1Plus and H1PlusPlus are the various hardware embodiments of the portable part of the present invention used for reading barcode and storing nutrition information. Operation with these various embodiments will now be described:

H1 Usage:
1. Swipe or scan bar or user defined code
2. System confirms valid code
3. Serving size prompt
4. Serving size select (end user may enter serving size information)
5. Time & date stamp applied
6. Device stores data (e.g. time, date, code, serving size)
7. Next food item is identified and the process starts over.

Additional feature includes a delete & clear option for when the user desires to delete or clear a scanned item, and two buttons for incrementing or decrementing the serving size information.

H1 Plus Usage

H1 Plus is used instead of H1 in order to view nutritional information, calculations, and or bench mark information in real time.
1. Swipe or scan bar or user defined code
2. System confirms valid code
3. Serving size prompt
4. Serving size select (end user may enter serving size information)
5. Time & date stamp applied
6. Device stores data (e.g. time, date, code, serving size)
7. Device displays calculated nutritional and other information (e.g. total calories, fats, sugar)
8. Next food item is identified and the process starts over
    Additional feature includes a delete & clear option for when the user desires to delete or clear a scanned item, and two buttons for incrementing or decrementing the serving size information.

H1PlusPlus Usage:

H1PlusPlus is used instead of H1 or H1Plus in order to view nutritional information, calculations, and or bench mark information in real time such as:
1. Device displays the optional daily or the total nutrition data in its journal along with its battery status, current date, time and temperature, on the LCD screen. Note: daily or total nutrition data may be disabled by the user in the set-up menu of the device.
2. While holding down the scan button, the user swipes or scans a bar or user defined code.
3. The device determines if a barcode is valid by verifying that the scanned code has a valid predefined length (e.g. 8 characters long) and type (e.g UPC, Code 128).
4. If code is valid, device applies time and date stamp to code and displays the scanned code. Otherwise, system is ready for rescan. Note: if the device is inactive for a predefined time, the device can optionally shut off automatically to save battery life. If device goes in to a sleep mode, no content will be lost and the user will be able to continue where he or she left off when the device is reactivated.
5. The device performs a search with its on-board database to find the scanned food code. If no code is found, the device will display that food information is not with its database (e.g. unknown food code). Otherwise, information such as image of product, product name and nutritional information are displayed.
    Note: The number of nutrition items displayed (e.g. sugar, calories, fat) are predefined by the user and are selectable during the database download from a host computer to the device memory.
6. The device prompts for confirmation. This step may also be disabled by the user in the set-up menu of the device.
7. If user agrees, the device prompts for serving size. Otherwise, device will go back to Step 2.
8. The user enters serving size information using the same interface buttons (e.g. 5-way joystick or buttons).
9. If the code is found, the device stores the serving size information, and displays the calculated nutrition food content and/or other information based on the serving size entered. If code is not found, this step is skipped.
10. To continue, the user acknowledges correct information is entered or system will go back to Step 8 to reenter the serving size information.
11. If the food code is found, the device displays the computed total nutritional content information or optional selected daily nutrition data. Otherwise, the device displays the last known total nutrition food content information and indicates that total is an estimate of what is in its journal (e.g. a bar or dot next to the total values).
12. The process starts from Step 3 for next food item ready to be scanned.

H2 is a third party or proprietary physical and/or wireless medium that can be used to download or transfer information collected from H1 to S2 or from S2 to H1. H2 connects to a personal computer that is running S1 and S2 software.
1. Connect H1 and S2 via standard or propriety communicating protocol or H2
2. Once handshake is established between H1 and S2, data is transferred from H1 to S2 or S2 to H1 via S1 data transfer routine
3. Upon data transfer from H1 to S1 and S2, data in H1 can be deleted H3 or third party hardware and operating system connects to H1 using a physical or wireless medium in order to retrieve collected codes from H1.
1. Connect H1 and H3 via standard or propriety communicating protocol or H2
2. Once handshake is established between H1 and H3, data is transferred from H1 to H3 or H3 to H1 via S1 or S2 data transfer routine
3. Upon data transfer from H1 to H3, the S2 database is used in order to match collected codes with food items and their corresponding nutritional content.

Residing in the H1 hardware, S1 can be used to manipulate, save, process, and store data downloaded or transferred data from H1 through H2

S2 or the client application/database retrieves nutritional information from S4 and matches this information with collected bar or user defined codes. S2 software performs the following:
1. Collect bar or user defined codes using H1, H1Plus, H1PlusPlus or H3.
2. Transfer collected codes to a personal computer, network, or H3 hardware via an S1, H2, or other connection and data transfer routine.
3. Once codes have been collected and transferred, S2 matches the codes with specific food items or meals.
4. Once food items and their corresponding codes have been matched, S2 enables the software, operating system, and hardware upon which it resides to display, manipulate, bench mark, process, and or print the food item or meals nutritional information.

S3 or user defined codes and food items software perform the following:
1. Identify food items or ingredients to be included in the user defined code.
2. Enter the food items nutritional content and serving size information into the S3 software.
3. The S3 software calculates the nutritional content of the combined food items by the specified serving size.
4. The S3 software next allows the user to name the food item.
5. The S3 software assigns a unique code to the food item which is printed by the user. This code is readable by H1, H1Plus, H1PlusPlus or a modified H3.
6. The S3 software sends the food item name, ingredients, nutritional content, and user defined code to the H5 server.
7. The H5 server makes the code and nutritional content information available to S2 users so that when the code is collected by H1, H1Plus, H1PlusPlus or H3, S2 will be able to recognize the food item, user defined name, and the corresponding nutritional content.

S4 is a server application/database that collects and stores FDA, industry, expert, restaurant, and user defined food items and user defined codes along with their corresponding nutritional content.
1. The S4 application database will store UPC, industry, restaurant, FDA, expert or user defined codes and their corresponding nutritional information. The S4 database also searches S2 databases, H7 and H8 hardware for new user defined food items and codes and their corresponding nutritional content.
2. S4 stores the collected information.
3. S4 makes this information available to S2 and/or S3 users during connections and data transfers between the various S2 and/or S3 users and S4.

H4 is a third party or proprietary physical or wireless medium that can be used to download or transfer information from H5 to the client or from the client to the server.
1. Connects H3 and H5 via a standard or propriety communicating protocol.
2. Once handshake is established between H3 and H5, data is transferred from H5 to H4 or H4 to H5 via S3 data transfer routine.

H5 is a third party hardware and software with operating system (e.g. workstation) where the S4 server application and database resides. Whenever communication is established between a S2 database and H5 via a H4 connection, a standard set of nutrition data and bar or user defined codes are transferred and uploaded between the server database and an S2 database.

S5 is an application that resides in the H7 hardware. Its purpose is to generate an internal barcode for each of the food items created by the users or from the food menus. Each new internal barcode along with its corresponding nutrition data are transferred to S4 database. For example:
1. Input a food item
2. Output (e.g. display on a screen or provides a hardcopy) a new internal barcode.
3. Ensure that the newly create internal barcode is not being used.
4. Stores the new internal barcode and its nutrition information.
5. Either push the new information to S4 server database or wait for the server to pull the newly created information.

H6 is a third party or proprietary physical or wireless medium that can be used to download or transfer information (e.g. code, nutrition information) from H7 to the server database using S5 software and/or from H6 to the server database using S4 software. For example:
1. Connects H5 and H7 and/or H8 via a standard or propriety communicating protocol.
2. Once handshake is established between H5 and H7, and/or H8, data is transferred from H8 and/or H7 to H5 using S5 and/or S4 data transfer routine respectively.

H7 is a third party hardware used to create and print out internal barcodes. In addition, it communicates and updates the S4 database servers with the new internal code and its nutrition food information when a new code is generated.

H8 represents third party web servers where the public food code and nutrition information resides. Whenever communication is established between a S4 database and H8 via a H6 connection, S4 software will continuously scan and monitor these web servers for updates. Once a change is identified, the S4 software will update its nutrition food database accordingly.

Several descriptions and illustrations have been provided to aid in understanding the present invention. One skilled in the art will realize that numerous changes and variations are possible without departing from the spirit of the invention. Each of these changes and illustrations is within the scope of the present invention.

We claim:

1. An electronic nutrition journal system comprising in combination:
   a server computer containing a master nutritional database, said database containing barcodes and nutritional data for a plurality of food items;
   wherein said server periodically accesses predetermined web sites to update said nutritional data;
   at least one portable handheld unit remote from said server computer, said portable handheld unit capable of scanning barcodes and recording serving sizes;
   said portable handheld unit in communication with said server either directly or through an intermediate computer, wherein said portable handheld unit can transfer barcodes scanned and recorded serving sizes to said server, and wherein said server or said intermediate computer can provide tracking of consumed nutrition values for an individual;
   and wherein said master nutritional database can be updated by adding new barcodes and associated nutritional values;
   and wherein application software running on said server can also update said master nutritional database by automatically visiting websites on the internet.

2. The electronic nutrition journal system of claim 1 wherein said portable handheld unit communicates wirelessly or over a partially wireless link with either said server or said intermediate computer.

3. The electronic nutrition journal system of claim 1 wherein said server can update said master nutritional database by receiving barcodes from a an external barcode generator located remotely from said server.

4. The electronic nutrition journal system of claim 3 wherein said server can update said master nutritional database by receiving food information from users via said network.

5. The electronic nutrition journal system of claim 3 wherein said external barcode generator receives food information from external sources of food information.

6. The electronic nutrition journal system of claim 3 wherein said external barcode generator is itself a fixed terminal or portable handheld unit.

7. The electronic nutrition journal system of claim 6 wherein said external barcode generator communicates with said server over the internet.

8. The electronic nutrition journal system of claim 1 wherein said intermediate computer is chosen from the group consisting of PC, laptop, PDA, cellular telephone and personal music player.

9. A method of providing an electronic nutrition journal comprising the steps of:
   providing a plurality of handheld personal units for use by users in reading barcodes on food items and entering serving sizes;
   providing a server containing a master nutritional database wherein barcodes are matched with nutritional content, wherein said server accesses a plurality of predetermined websites to update said master nutritional database;
   using food and serving data from one of said handheld personal units in cooperation with said master nutritional database to provide tracking of personal nutrition consumption.

10. The method of providing an electronic nutrition journal of claim 9 further comprising the step of causing said server to receive food menu input from users.

11. The method of providing an electronic nutrition journal of claim 9 further comprising the step of causing said server to receive food menu input from external sources of food information.

12. The method of providing an electronic nutrition journal of claim 9 further comprising an external barcode generator.

13. The method of providing an electronic nutrition journal of claim 9 wherein at least one of said handheld personal units communicates with said server through an intermediate computer.

14. The method of providing an electronic nutrition journal of claim 13 wherein said handheld personal unit communicates with said intermediate computer wirelessly or over a link that is partially wireless.

15. An electronic nutritional journal comprising at least one handheld unit capable of recording food intake data in communication with an intermediate computer or with a server, said intermediate computer or server containing a master nutritional database, said master nutritional database relating food intake to nutritional values, and wherein said intermediate computer or said server provides tracking of an individual's nutritional intake, and further wherein said intermediate computer or said server can update said master nutritional database by visiting at least one website remote to said intermediate computer or server, and wherein said server contains web-crawling software to search for websites containing nutritional information.

16. The electronic nutritional journal of claim 15 wherein said master nutritional database can also be updated by receiving food information from users.

17. The electronic nutritional journal of claim 15 wherein said master nutritional database can also be updated by receiving food information from external sources of food information.

18. The electronic nutritional journal of claim 15 wherein said intermediate computer is chosen from the group consisting of PC, laptop, PDA, cellular telephone and personal music device.

19. The electronic nutritional journal of claim 15 wherein said intermediate computer or said server receives information from an external barcode generator.

20. The electronic nutritional journal of claim 19 wherein said external barcode generator receives information from external sources of food information.

21. An electronic nutritional journal comprising at least one handheld unit capable of recording food intake data in communication with an intermediate computer or with a server , said intermediate computer or server containing a master nutritional database, said master nutritional database relating food intake to nutritional values, and wherein said intermediate computer or said server provides tracking of an individual's nutritional intake, and further wherein said intermediate computer or said server can update said master nutritional database by receiving food information input from a plurality of predetermined websites.

* * * * *